United States Patent [19]

Bensinger

[11] Patent Number: 4,614,513
[45] Date of Patent: Sep. 30, 1986

[54] METHOD AND APPARATUS FOR TREATMENT TO REMOVE IMMUNOREACTIVE SUBSTANCES FROM BLOOD

[75] Inventor: William I. Bensinger, Seattle, Wash.

[73] Assignee: Fred Hutchinson Cancer Research Center, Seattle, Wash.

[21] Appl. No.: 639,727

[22] Filed: Aug. 13, 1984

[51] Int. Cl.[4] .............................................. A61M 1/03
[52] U.S. Cl. ...................................... 604/6; 210/651; 128/DIG. 3
[58] Field of Search ................. 128/DIG. 3; 210/295, 210/321.1, 433.2, 650–651

[56] References Cited

U.S. PATENT DOCUMENTS

| | | | |
|---|---|---|---|
| 3,995,018 | 11/1976 | Sjöquist | 424/1.5 |
| 4,215,688 | 2/1979 | Terman et al. | 604/5 |
| 4,381,004 | 4/1983 | Babb | 604/5 |
| 4,464,165 | 8/1984 | Pollard | 604/5 |

OTHER PUBLICATIONS

"Covalent Coupling Methods for Inorganic Support Materials", Howard H. Weetall, pp. 134–148.
"A Procedure for Removing High Titer Antibodies by Extracorporeal Protein-A-Sepharose Adsorption in Hemophilia: Substitution Therapy and Surgery in a Patient with Hemophilia B and Antibodies", Inga Marie Nilsson et al., *Blood*, vol. 58, No. 1, Jul. 1981, pp. 38–44.
"Specific Immunoadsorption of IgG Antibody in a Patient with Chronic Lymphocytic Leukemia and Autoimmune Hemolytic Anemia", E. C. Besa et al., *The American Journal of Medicine*, Dec. 1981, vol. 71, p. 1035.
"Ex Vivo Removal of Serum IgG in a Patient with Colon Carcinoma", S. C. Bansal, M.D. et al., *Cancer*, vol. 42, No. 1, Jul. 1978, pp. 1–18.
"Treatment of Feline Lymphosarcoma by Extracorporeal Immunosorption", F. R. Jones, et al., pp. 235–243.
"Treatment of Advanced Malignancy with Plasma Perfused Over Staphylococcal Protein A", F. R. MacKintosh et al., *The Western Journal of Medicine*, Jul. 1983, p. 36.
"Phase I Trial of Staphylococcus aureus Cowan I Immunoperfusion", G. L. Messerschmidt et al., *Cancer Treatment Reports*, Dec. 1982, vol. 66, No. 12, p. 2027.
"Treatment of Feline Leukemia and Reversal of FeLV by Ex Vivo Removal of IgG", F. R. Jones et al., *Cancer*, 1980, vol. 46, No. 4, pp. 675–684.
"Preliminary Observations of the Effects on Breast Adenocarcinoma of Plasma Perfused Over Immobilized Protein A", D. S. Terman et al., *New England Journal of Medicine*, Nov. 12, 1981, vol. 305, No. 20, pp. 1195–1200.
"Plasma Perfused Over Immobilized Protein A for Breast Cancer", (letter) W. I. Bensinger, et al., *New England Journal of Medicine*, Apr. 15, 1982, vol. 306, No. 15.
"Extracorporeal Perfusion of Plasma Over Immobilized Protein A in Patient with Kaposi's Sarcoma and Acquired Immunodeficiency", D. D. Kiprov et al., *Journal of Biological Response Modifiers*, in press, pp. 341–346.

*Primary Examiner*—Dalton L. Truluck
*Attorney, Agent, or Firm*—Christensen, O'Connor, Johnson & Kindness

[57] ABSTRACT

A method and apparatus are disclosed for treating a patient by removing immunoreactive substances from the patient's blood using microbial ligands such as Staphylococcus Protein A. The method of the present invention comprises removing blood from the patient, separating the removed blood into plasma and cellular components, passing the plasma component through an immunoadsorbent material to produce a treated plasma component, and returning the treated plasma component and the cellular component to the patient. The immunoadsorbent material comprises a microbial ligand such as Staphylococcus Protein A, or components thereof, covalently bonded to an inert and nondegradable support. The removing, separating, passing and returning steps are performed substantially continuously and simultaneously with one another. The immunoadsorbent material may comprise one to three milligrams of the microbial ligand for each gram of support, and about 20–40 ml of the plasma component may be passed through the immunoadsorbent material per minute. In one preferred embodiment, the immunoadsorbent material comprises Staphylococcus Protein A, or components thereof, that have been covalently bonded to a silica support by first coating the silica support with an alkylamine and then coupling Staphylococcus Protein A to the alkylamine by means of a carbodiimide.

8 Claims, 2 Drawing Figures

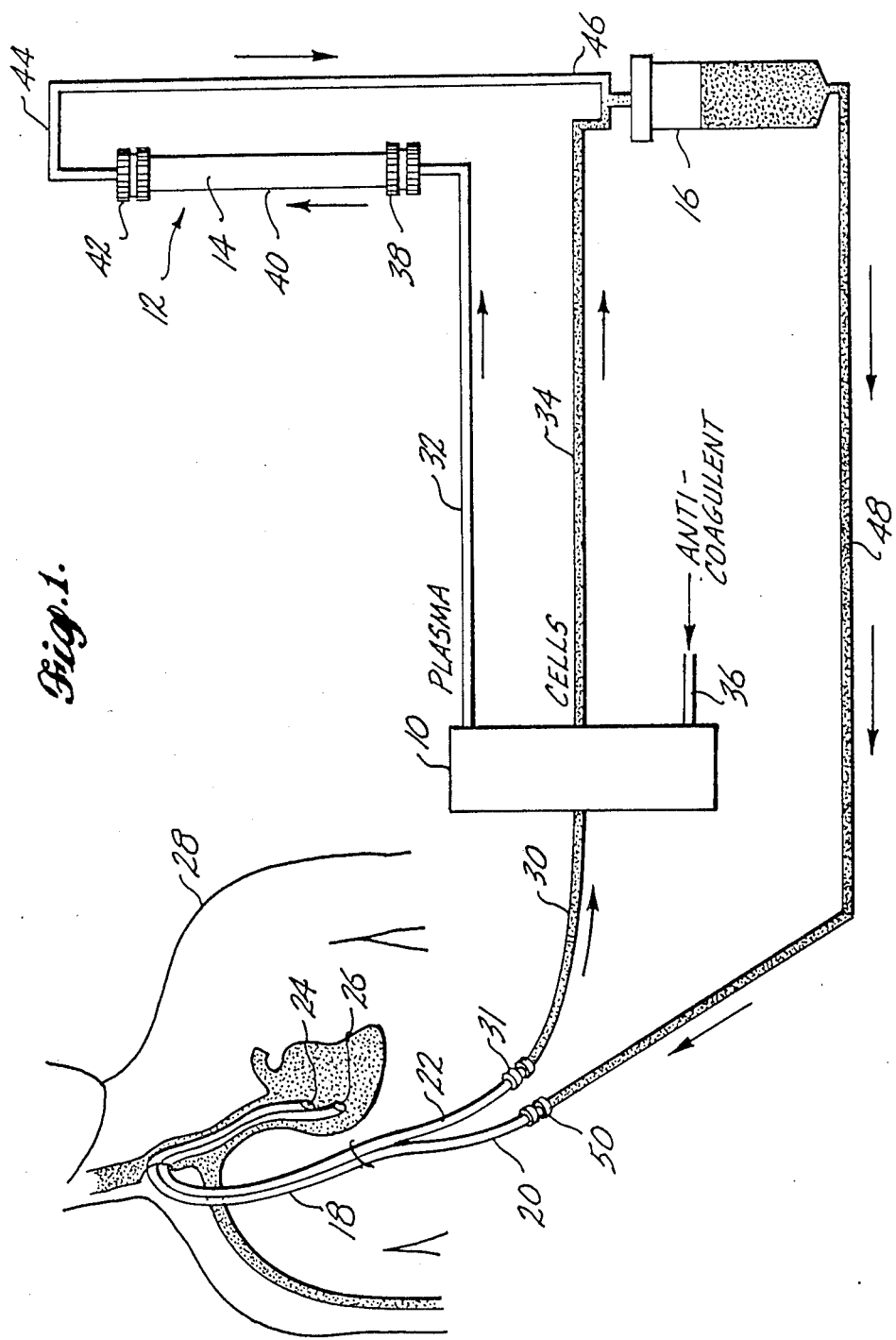

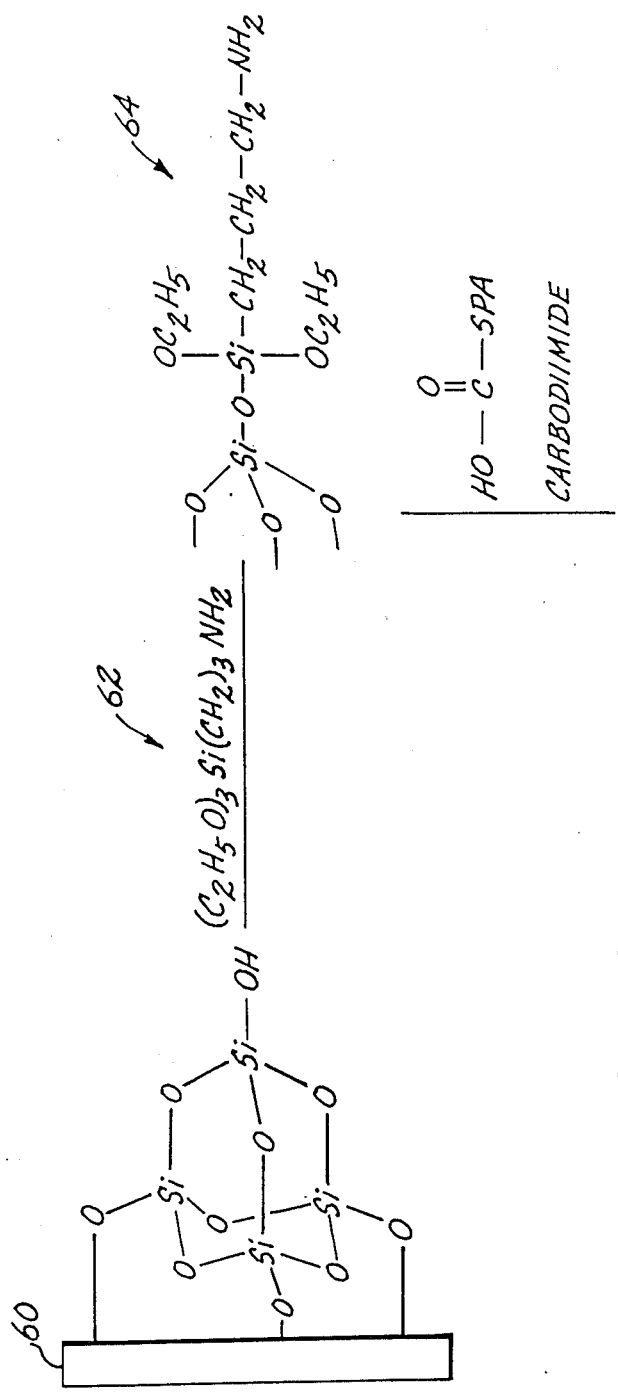

METHOD AND APPARATUS FOR TREATMENT TO REMOVE IMMUNOREACTIVE SUBSTANCES FROM BLOOD

GOVERNMENT RIGHTS

This invention was made with Government support under Grant No. CA 18579 awarded by the National Cancer Institute. The Government has certain rights in this invention.

FIELD OF THE INVENTION

The present invention relates to a method and apparatus for the treatment of cancer and immunologic disorders. The treatment involves removing immunoreactive substances from blood using a plasmapheresis technique.

BACKGROUND OF THE INVENTION

Most tumors include associated antigens that are capable of inducing an immune response in their hosts. Despite this immune response, tumors generally continue to grow in vivo. The presence of circulating immune complexes in the plasma of tumor hosts has suggested one possible explanation to this paradox. Although the role of circulating immune complexes remains uncertain, it has been established that Staphylococcus Protein A (SPA), a molecule found in the wall of certain strains of Staphylococcus aureus, can adsorb the circulating immune complexes in the plasma of tumor bearing hosts.

Previous techniques for bringing a host's blood into contact with SPA have involved removing blood from the host, separating the removed blood into plasma and cellular components, and bringing the plasma into contact with heat-killed Staphylococcus aureus, or with a collodion-charcoal support to which SPA was mechanically bound. All such techniques have been found to produce significant undesirable side effects in human patients. The use of a collodion-charcoal support possesses the further disadvantages that only minute amounts of SPA can be mechanically bound to such a support, and that SPA rapidly leaches off the support during use.

SUMMARY OF THE INVENTION

The present invention provides a method and apparatus for treating a patient by removing immunoreactive substances from the patient's blood using microbial ligands such as Staphylococcus Protein A.

In one aspect, the present invention provides a method for treating a patient by removing immunoreactive substances from the patient's blood. The method comprises removing blood from the patient, separating the removed blood into plasma and cellular components, and then passing the plasma component through an immunoadsorbent material comprising microbial ligands covalently bonded to an inert support. The plasma component, after treatment with the immunoadsorbent material, is returned together with the cellular component to the patient. The removing, separating, passing and returning steps are performed substantially continuously and simultaneously with one another. The microbial ligand preferably comprises at least components of Staphylococcus Protein A, i.e., Staphylococcus Protein A or components thereof. The immunoadsorbent material may comprise one to three milligrams of the microbial ligand for each gram of the support. The mass of the support is preferably about 100 grams, and the flow rate of the plasma component through the immunoadsorbent material is preferably 20–40 ml/minute. The microbial ligand may be bonded to the support by means of an alkylamine linkage, and the immunoadsorbent material may comprise a microbial ligand that has been covalently bonded to a silica support by first coating the silica support with an alkylamine and then coupling the microbial ligand to the alkylamine by means of a carbodiimide.

In another aspect, the present invention provides an apparatus for treating a patient by removing immunoreactive substances from the patient's blood. The apparatus comprises means for removing a continuous flow of blood from the patient, means for continuously separating the removed blood into plasma and cellular components, means for continuously passing the plasma component through an immunoadsorbent material to thereby produce a treated plasma component, and means for returning the cellular component and the treated plasma component to the patient. The immunoadsorbent material comprises a microbial ligand, such as Staphylococcus Protein A or components of Staphylococcus Protein A, covalently bonded to an inert support.

BRIEF DESCRIPTION OF THE DRAWINGS

FIG. 1 is a schematic diagram of an apparatus for treating a patient that may be used for carrying out the present invention.

FIG. 2 is a schematic diagram of a preferred method of covalently bonding SPA to a silica support.

DETAILED DESCRIPTION OF THE INVENTION

FIG. 1 illustrates one preferred apparatus for treating a patient so as to remove immunoreactive substances such as immunoglobulins, immune complexes and antibodies from the patient's blood. The apparatus includes plasma separator 10, a column 12 filled with an immunoadsorbent material 14, drip chamber 16 and catheter 18. In the illustrated embodiment, catheter 18 comprises a double-lumen central venous catheter that includes inlet conduit 20 and outlet conduit 22 whose respective ends 24 and 26 are adapted for insertion into the circulatory system of patient 28. Other known methods of blood access, such as arteriovenous shunts, fistulas, or double venipuncture, may also be used. Outlet conduit 22 of catheter 18 is coupled by connector 31 to tube 30 such that whole blood from patient 28 flows from the outlet conduit, through tube 30, and into plasma separator 10.

Plasma separator 10 may comprise any suitable device for separating whole blood into plasma and cellular components. Examples of suitable plasma separators include continuous flow cell centrifuges, flat sheet membrane devices and hollow fiber membrane devices. The plasma component of the patient's blood flows out of plasma separator 10 through tube 32, and the cellular component of the patient's blood flows out of the plasma separator through tube 34. A suitable anticoagulant, such as heparin, is provided to the plasma separator through inlet 36 to prevent clotting.

The plasma component flows from tube 32 into the lower end of column 12. Column 12 comprises cylinder 40, lower fitting 38 and upper fitting 42. The interior of the column is packed with immunoadsorbent material 14, described below, that selectively absorbs immunoreactive substances from the plasma component. Column 12 also includes screens (not shown) associated with the lower and upper fittings to contain the immunoadsorbent material in the column while allowing free passage of the plasma component. 300 mesh stainless steel screens have been found to be suitable. The plasma component flows from tube 32 through lower fitting 38, upward through immunoadsorbent material 14, and the treated plasma component then exits from column 12 through upper fitting 42 into tube 44.

The cellular component in tube 34 and the treated plasma component in tube 44 flow through connector 46 into drip chamber 16, where they are allowed to mix and flow out of the drip chamber through tube 48. Tube 48 is joined by connector 50 to inlet conduit 20 of catheter 18, and the reconstituted blood in tube 48 therefore flows back to the patient through the inlet conduit.

Immunoadsorbent material 14 of column 12 comprises an inert support to which a microbial ligand has been covalently bonded. A preferred microbial ligand is Staphylococcus Protein A (SPA). The inert support may comprise, silica, glass, plastic, or any other nonreactive and nondegradable material, and may be in the shape of beads or in other suitable shapes. SPA may be used either in its whole form, or in the form of purified components that include the binding site for immunoreactive substances. A preferred technique for linking the microbial ligand to the support is to first coat the support material with an alkylamine silane such as γ-aminopropyltriethoxysilane, and to then link the amino silanated support material to the ligand by means of a coupling reagent such as a carbodiimide, glutaraldehyde, or an acid chloride.

In the case where the inert support comprises silica, it has been found that a particularly advantageous and preferred method of bonding a ligand such as SPA to the support is by means of a carbodiimide coupling reagent. In the carbodiimide coupling technique, an alkylamine is bonded to the surface of the silica beads, and the alkylamine is then coupled to a carboxyl group of SPA by means of a carbodiimide. These steps are illustrated schematically in FIG. 2. In FIG. 2, numeral 60 represents a portion of a silica bead whose surface includes a matrix of silicon and oxygen atoms. The silica is reacted, preferably in an aqueous, acidic medium, with γ-aminopropyltriethoxysilane to form complex 64 in which the alkylamine silane is bonded directly to the silica. Complex 64 is then reacted with SPA in the presence of a suitable carbodiimide. The carbodiimide causes the carboxyl groups of the SPA molecule to condense with the amino groups of complex 64 to form structure 66 in which the SPA molecules are covalently bonded to the silica through alkylamine linkages.

The SPA is preferably coupled to the support at a density of about 1–3 milligrams per gram of support, and even more preferably at a density of about 2 milligrams of SPA for each gram of support. This density can be readily achieved using a silica support and the carbodiimide coupling technique described above, and has been found to give the highest binding activity for immunoadsorbent material 14. Column 12 may contain about 100 grams of such material, resulting in a column containing 100–300 milligrams of SPA, a quantity much higher than that obtainable with mechanical immobilization techniques such as those based upon collodion-charcoal. The flow rate of plasma through the column is preferably maintained in the range of 20–40 ml/minute.

In a typical treatment session, one plasma volume of a patient is passed through column 12. Such treatment sessions are preferably performed 2–3 times per week for a minimum of eight weeks. The treatment technique of the present invention has resulted in antitumor effects in patients with adenocarcinoma and in patients with melanoma. In contrast to prior techniques involving plasma perfusion over whole Staphylococcus aureus or over microbial ligands such as SPA, no excessive toxic side effects were observed in any such patients.

While the preferred embodiments of the invention have been illustrated and described, it should be understood that variations will be apparent to those skilled in the art. Accordingly, the invention is not to be limited to the specific embodiments illustrated and described, and the true scope and the spirit of the invention are to be determined by reference to the appended claims.

The embodiments of the invention in which an exclusive property or privilege is claimed are defined as follows:

1. A method for treating a patient by removing immunoreactive substances from the patient's blood, comprising:

removing blood from the patient;

separating the removed blood into a plasma component and a cellular component;

passing the plasma component through an immunoadsorbent material comprising a microbial ligand covalently bonded to an inert support to thereby produce a treated plasma component, the immunoadsorbent material comprising from one to three milligrams of the microbial ligand for each gram of the inert support, the microbial ligand comprising at least components of Staphylococcus Protein A; and returning the cellular component and the treated plasma component to the patient;

the removing, separating, passing and returning steps being performed substantially continuously and simultaneously with one another.

2. The method of claim 1, wherein the immunoadsorbent material comprises about two milligrams of the microbial ligand for each gram of the inert support.

3. The method of claim 1, wherein the mass of the immunoadsorbent material is about 100 grams.

4. A method for treating a patient by removing immunoreactive substances from the patient's blood, comprising:

removing blood from the patient;

separating the removed blood into a plasma component and a cellular component;

passing the plasma component through an immunoadsorbent material comprising a microbial ligand that has been covalently bonded to a silica support by first coating the silica support with an alkylamine and then coupling the microbial ligand to the alkylamine by means of a carbodiimide to thereby produce a treated plasma component, the microbial ligand comprising at least components of Staphylococcus Protein A;

returning the cellular component and the treated plasma component to the patient; and the removing, separating, passing and returning steps being performed substantially continuously and simultaneously with one another.

5. An apparatus for treating a patient by removing immunoreactive substances from the patient's blood, comprising:

means for removing a continuous flow of blood from the patient;

means for continuously separating the removed blood into a plasma component and a cellular component;

means for continuously passing the plasma component through an immunoadsorbent material comprising a microbial ligand covalently bonded to an inert support to thereby produce a treated plasma component, the immunoadsorbent material comprising from one to three milligrams of the microbial ligand for each gram of the inert support, the microbial ligand comprising at least components of Staphylococcus Protein A; and means for returning the cellular component and the treated plasma component to the patient.

6. The apparatus of claim 5, wherein the immunoadsorbent material comprises about two milligrams of the microbial ligand for each gram of the inert support.

7. The apparatus of claim 5, wherein the mass of the immunoadsorbent material is about 100 grams.

8. An apparatus for treating a patient by removing immunoreactive substances from the patient's blood, comprising:

means for removing a continuous flow of blood from the patient;

means for continuously separating the removed blood into a plasma component and a cellular component;

means for continuously passing the plasma component through an immunoadsorbent material comprising a microbial ligand that has been covalently bonded to a silica support by first coating the silica support with an alkylamine and then coupling the microbial ligand to the alkylamine by means of a carbodiimide, to thereby produce a treated plasma component, the microbial ligand comprising at least components of Staphylococcus Protein A; and means for returning the cellular component and the treated plasma component to the patient.

* * * * *